(12) United States Patent
Nakayama

(10) Patent No.: US 7,791,039 B2
(45) Date of Patent: Sep. 7, 2010

(54) RADIATION IMAGE CAPTURING APPARATUS AND METHOD OF DETECTING MALFUNCTION OF RADIATION IMAGE CAPTURING APPARATUS

(75) Inventor: Hiroki Nakayama, Aiko-gun (JP)

(73) Assignee: FUJIFILM Corporation, Tokyo (JP)

( * ) Notice: Subject to any disclaimer, the term of this patent is extended or adjusted under 35 U.S.C. 154(b) by 85 days.

(21) Appl. No.: 12/049,664

(22) Filed: Mar. 17, 2008

(65) Prior Publication Data
US 2008/0224047 A1 Sep. 18, 2008

(30) Foreign Application Priority Data
Mar. 16, 2007 (JP) ............... 2007-068092

(51) Int. Cl.
*G01T 1/00* (2006.01)
(52) U.S. Cl. ......................... 250/393; 378/97
(58) Field of Classification Search .................. 250/393; 378/97
See application file for complete search history.

(56) References Cited

U.S. PATENT DOCUMENTS 5,751,783 A 5/1998 Granfors et al.

6,151,383 A * 11/2000 Xue et al. ............... 378/108

FOREIGN PATENT DOCUMENTS

| JP | 10-284289 A | 10/1998 |
|---|---|---|
| JP | 2004-154409 A | 6/2004 |

* cited by examiner

*Primary Examiner*—David P Porta
*Assistant Examiner*—Shun Lee
(74) *Attorney, Agent, or Firm*—Sughrue Mion, PLLC

(57) ABSTRACT

A mammographic system as a radiation image capturing apparatus includes a radiation source for emitting radiation, a solid-state detector for detecting radiation emitted from the radiation source and generating a radiation image based on such radiation, AEC sensors for detecting a radiation dose emitted from the radiation source, a radiation source controller for controlling the dose emitted from the radiation source based on output signals from the AEC sensors, a reference output storage unit for storing reference output ranges defining respective ranges of reference output signals for the solid-state detector and the AEC sensors, and a malfunction detector for comparing output signals generated by the solid-state detector and the AEC sensors with the respective reference output ranges to detect a malfunction of the solid-state detector, the AEC sensors, or the radiation source.

5 Claims, 8 Drawing Sheets

RADIATION IMAGE CAPTURING APPARATUS AND METHOD OF DETECTING MALFUNCTION OF RADIATION IMAGE CAPTURING APPARATUS

BACKGROUND OF THE INVENTION

1. Field of the Invention

The present invention relates to a radiation image capturing apparatus including a malfunction detecting means for detecting a malfunction of a radiation image generating means, a radiation dose information detector, or a radiation source. The present invention also relates to a method of detecting a malfunction of such a radiation image capturing apparatus.

2. Description of the Related Art

In the medical field, there have widely been used radiation image capturing apparatuses, which apply radiation emitted from a radiation source to a subject. Such apparatus then detect the radiation that has passed through the subject with a radiation detector, and record radiation image information based on the detected radiation.

The radiation image capturing apparatuses of the type described above are required to achieve a good level of radiation image quality, while minimizing the radiation dose applied to the subject (patient). In order to acquire appropriate radiation image information of a region of interest (ROI), it is necessary to establish an exposure control condition, for the purpose of applying a desired dose of radiation to the region of interest.

Japanese Laid-Open Patent Publication No. 10-284289 discloses an X-ray system including an AEC (Automatic Exposure Control) sensor (radiation dose information detector) serving as a detector for automatic exposure control, which is disposed behind a solid-state detector (radiation image generating means) for detecting radiation emitted from a radiation source and generating a radiation image based on the detected radiation. The dose of radiation emitted from the radiation source is controlled based on the radiation dose detected by the AEC sensor.

Radiation detectors, including the solid-state detector and the AEC sensor used in the radiation image capturing apparatus, may possibly suffer from sensitivity malfunctions characterized by fluctuations of an output value thereof (an output signal level or an output current value) with respect to an expected value. Alternatively, the radiation detectors may have normal sensitivity, but the radiation source may possibly suffer from output malfunctions.

These malfunctions may reliably be detected and specified by a separate instrument such as a radiation dosimeter or the like, for example, for measuring the radiation output level. However, if an existing radiation image capturing apparatus does not incorporate such a radiation dosimeter therein, then the radiation image capturing apparatus will require extra expenditures of expense and time in order to connect and adjust the added radiation dosimeter. A radiation image capturing apparatus with a built-in radiation dosimeter, however, is costly due to the presence of the built-in radiation dosimeter.

SUMMARY OF THE INVENTION

A general object of the present invention is to provide a radiation image capturing apparatus, which is capable of detecting a malfunction of a radiation image generating means, a radiation dose information detector, or a radiation source, without the need for a separate instrument such as a radiation dosimeter or the like, together with a method of detecting a malfunction in such a radiation image capturing apparatus.

According to an aspect of the present invention, a radiation image capturing apparatus includes a malfunction detector for comparing output signals generated by a radiation image generating means and a radiation dose information detector based on a radiation emitted from a radiation source, with stored respective reference output ranges, in order to detect a malfunction of any of the radiation image generating means, the radiation dose information detector, or the radiation source. It is possible to detect a malfunction of any of the radiation image generating means, the radiation dose information detector, or the radiation source, easily and inexpensively without the need for a separate instrument such as a radiation dosimeter or the like.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

A radiation image capturing apparatus, and a method of detecting a malfunction in a radiation image capturing apparatus, according to preferred embodiments of the present invention shall be described in detail below with reference to the accompanying drawings.

Figure 1:
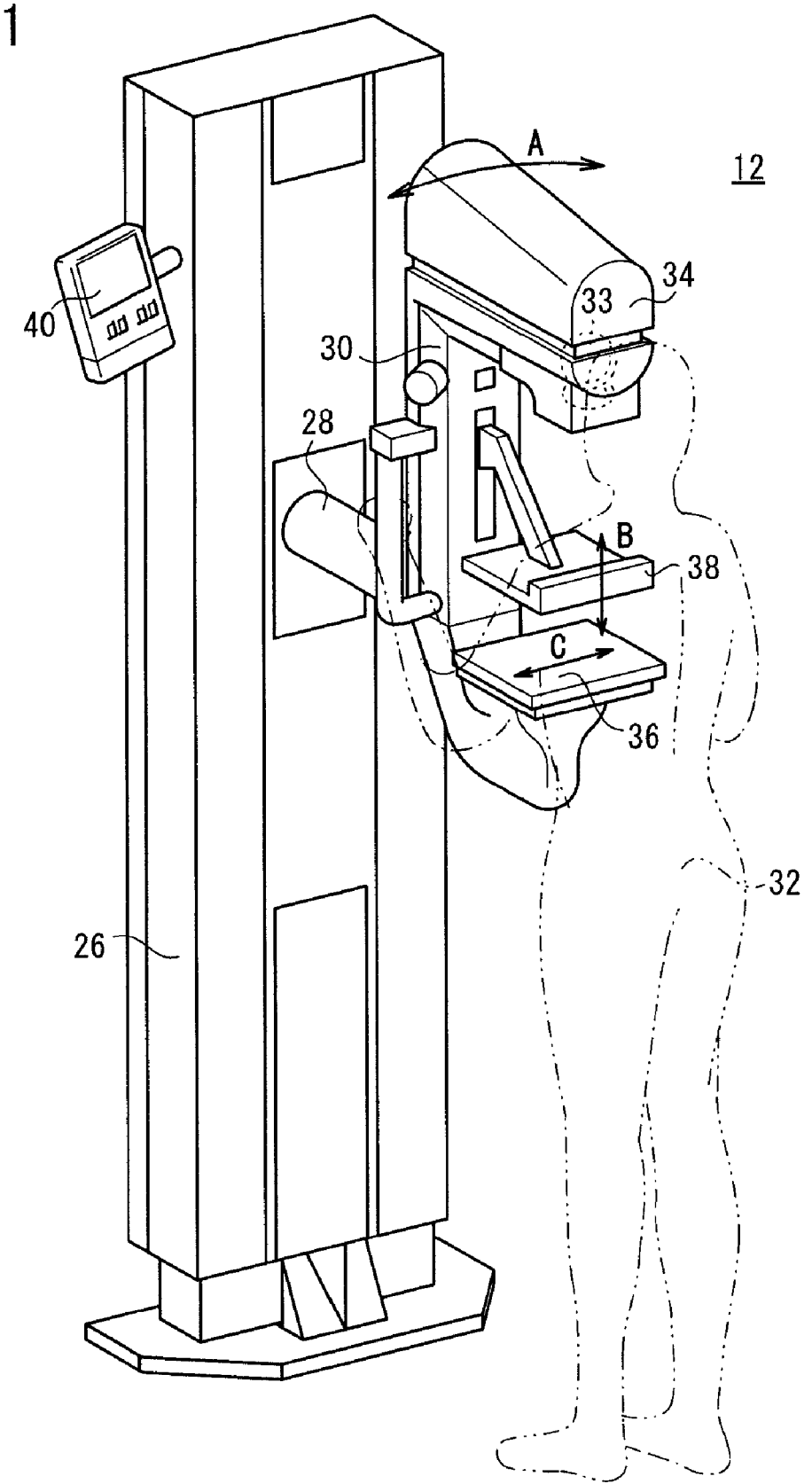
FIG. 1 is a perspective view of a mammographic system, as an example of a radiation image capturing apparatus according to an embodiment of the present invention.

FIG. 1 shows in perspective a mammographic system 12 as an example of a radiation image capturing apparatus according to an embodiment of the present invention. Although a mammographic system 12 will be described below as exemplifying the radiation image capturing apparatus according to the embodiment of the present invention, the present invention is not limited to a mammographic system 12.

As shown in FIG. 1, the mammographic system 12 includes an upstanding base 26, a vertical arm 30 fixed to a horizontal swing shaft 28 disposed substantially centrally on the base 26, a radiation source housing unit 34 storing a radiation source 33 for applying radiation to a breast of a subject 32 to be imaged, and which is fixed to an upper end of the arm 30, an image capturing base 36 disposed in vertically confronting relation to the radiation source housing unit 34 and fixed to a lower end of the arm 30, and a compression plate 38 for compressing and holding the breast against the image capturing base 36. The image capturing base 36 houses therein a solid-state detector (a radiation image generating means or an image sensor) 46 (see FIG. 2) for detecting radiation that has passed through the breast and for generating a radiation image based on the detected radiation.

When the arm 30, to which the radiation source housing unit 34 and the image capturing base 36 are secured, is angularly moved about the swing shaft 28 in the directions indicated by the arrow A, an image capturing direction with respect to the breast of the subject 32 is adjusted. The compression plate 38 that is coupled to the arm 30 is disposed between the radiation source housing unit 34 and the image capturing base 36. The compression plate 38 is vertically displaceable along the arm 30 in the directions indicated by the arrow B.

To the base 26, there is connected a display control panel 40 for displaying image capturing information including an image capturing region, an image capturing direction, etc., of the subject 32 that is detected by the mammographic apparatus 20, ID information of the subject 32, etc., and settings for these items of information, if necessary.

Figure 2:
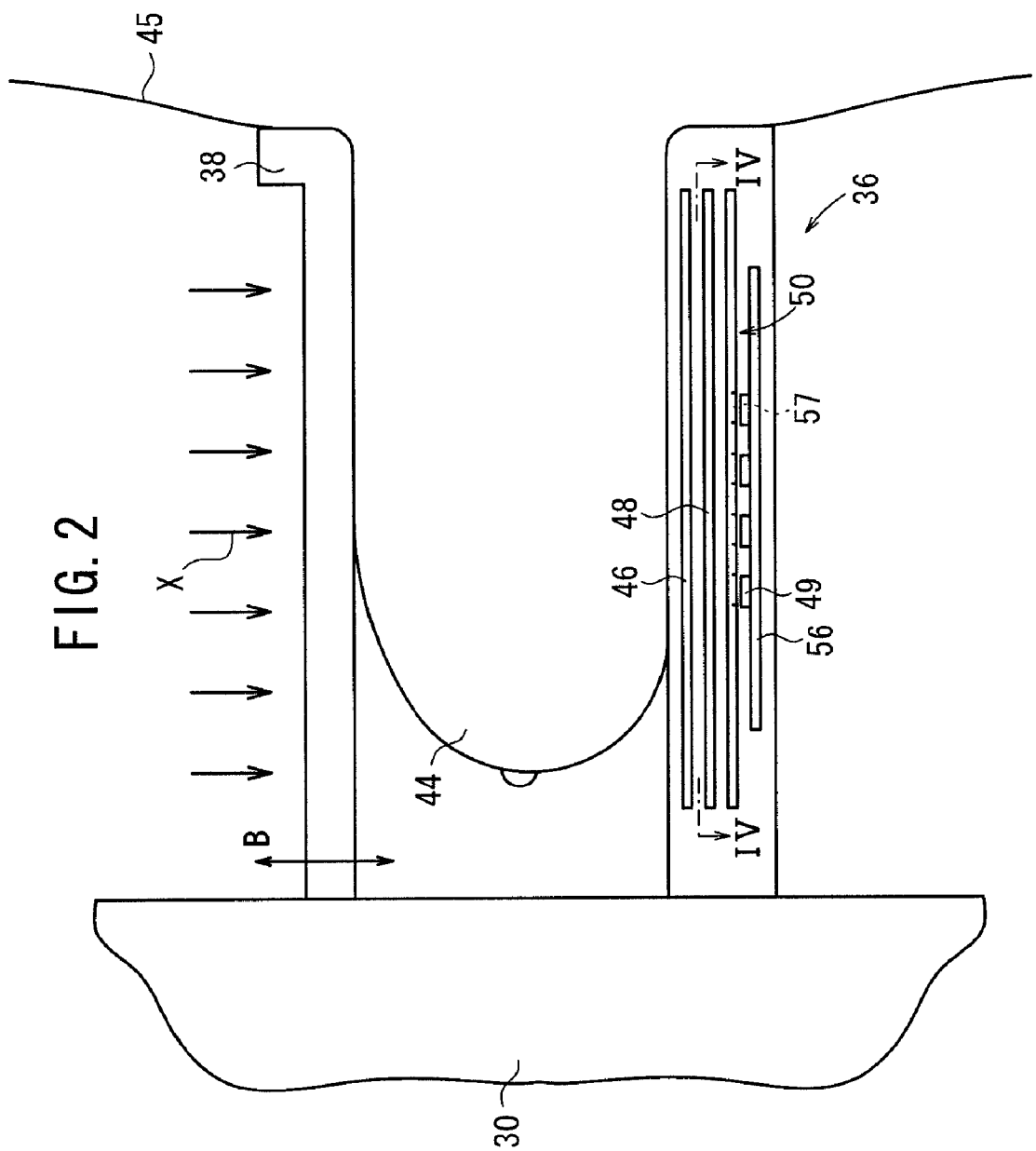
FIG. 2 is a fragmentary vertical elevational view, partially in cross section, showing internal structural details of an image capturing base of the mammographic system shown in FIG. 1.

FIG. 2 shows internal structural details of the image capturing base 36 of the mammographic apparatus 20. In FIG. 2, the breast, denoted by 44, of the subject 32 is shown as being placed between the image capturing base 36 and the compression plate 38. Reference numeral 45 represents the chest wall of the subject 32.

The image capturing base 36 houses therein a solid-state detector 46 for storing radiation image information, which has been captured based on radiation X that has been emitted from the radiation source 33 housed in the radiation source housing unit 34, and for outputting the stored radiation image information as an electric signal to generate a radiation image, and a reading light source 48 for applying reading light to the solid-state detector 46 in order to read the radiation image information stored in the solid-state detector 46. The image capturing base 36 also houses therein a plurality of radiation dose information detectors (hereinafter referred to as AEC sensors 49) for detecting the radiation dose of radiation X that has passed through the breast 44 and the solid-state detector 46, in order to determine exposure (irradiation) control conditions for the radiation X. Further, the image capturing base 36 houses therein an erasing light source 50 for applying erasing light to the solid-state detector 46, so as to remove unwanted electric charges stored in the solid-state detector 46.

The solid-state detector 46, which serves as a radiation image generating means, comprises a direct-conversion, light-reading radiation solid-state detector, for example. The solid-state detector 46 stores radiation image information therein as an electrostatic latent image, based on the radiation X that has passed through the breast 44, and generates an electric current depending on the electrostatic latent image when the solid-state detector 46 is scanned by reading light applied from the reading light source 48.

The solid-state detector 46 may be a detector such as that disclosed in Japanese Laid-Open Patent Publication No. 2004-154409, for example. More specifically, the solid-state detector 46 comprises a laminated assembly made up of a first electrically conductive layer disposed on a glass substrate for passing the radiation X therethrough, a recording photoconductive layer for generating electric charges upon exposure to the radiation X, a charge transport layer, which acts substantially as an electric insulator with respect to latent image polarity electric charges developed in the first electrically conductive layer, and which acts substantially as an electric conductor with respect to transport polarity charges that are of a polarity opposite to the latent image polarity electric charges, a reading photoconductive layer for generating electric charges and becoming electrically conductive upon exposure to the reading light, and a second electrically conductive layer permeable to the radiation X. An electric energy storage region is provided at the interface between the recording photoconductive layer and the charge transport layer.

Each of the first electrically conductive layer and the second electrically conductive layer provides an electrode. The electrode provided by the first electrically conductive layer comprises a two-dimensional flat electrode. The electrode provided by the second electrically conductive layer comprises a plurality of linear electrodes, spaced at a predetermined pixel pitch, for detecting radiation image information of the radiation image to be recorded as an image signal. The linear electrodes are arranged in an array along a main scanning direction, and extend in an auxiliary scanning direction perpendicular to the main scanning direction.

The reading light source 48 includes, for example, a line light source comprising a linear array of LED chips, and an optical system for applying a line of reading light emitted from the line light source to the solid-state detector 46. The linear array of LED chips extends perpendicularly to a direction in which the linear electrodes of the second electrically conductive layer of the solid-state detector 46 extend. The line light source moves along directions (i.e., the directions indicated by the arrow C in FIG. 3) in which the linear electrodes extend, so as to expose and scan the entire surface of the solid-state detector 46.

Figure 3:
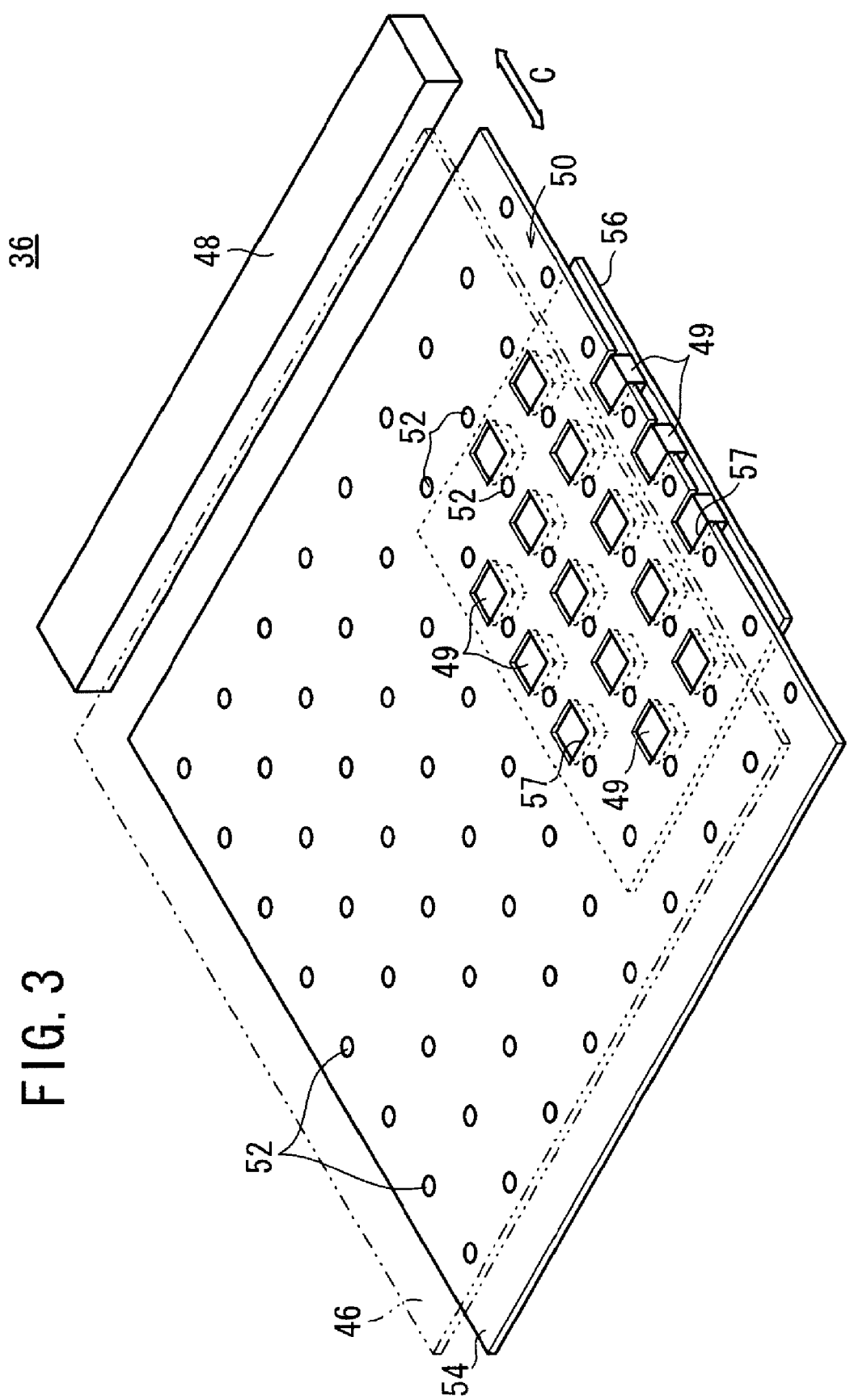
FIG. 3 is a perspective view, partially omitted from illustration, of the internal structural details of the image capturing base shown in FIG. 2.
Figure 4:
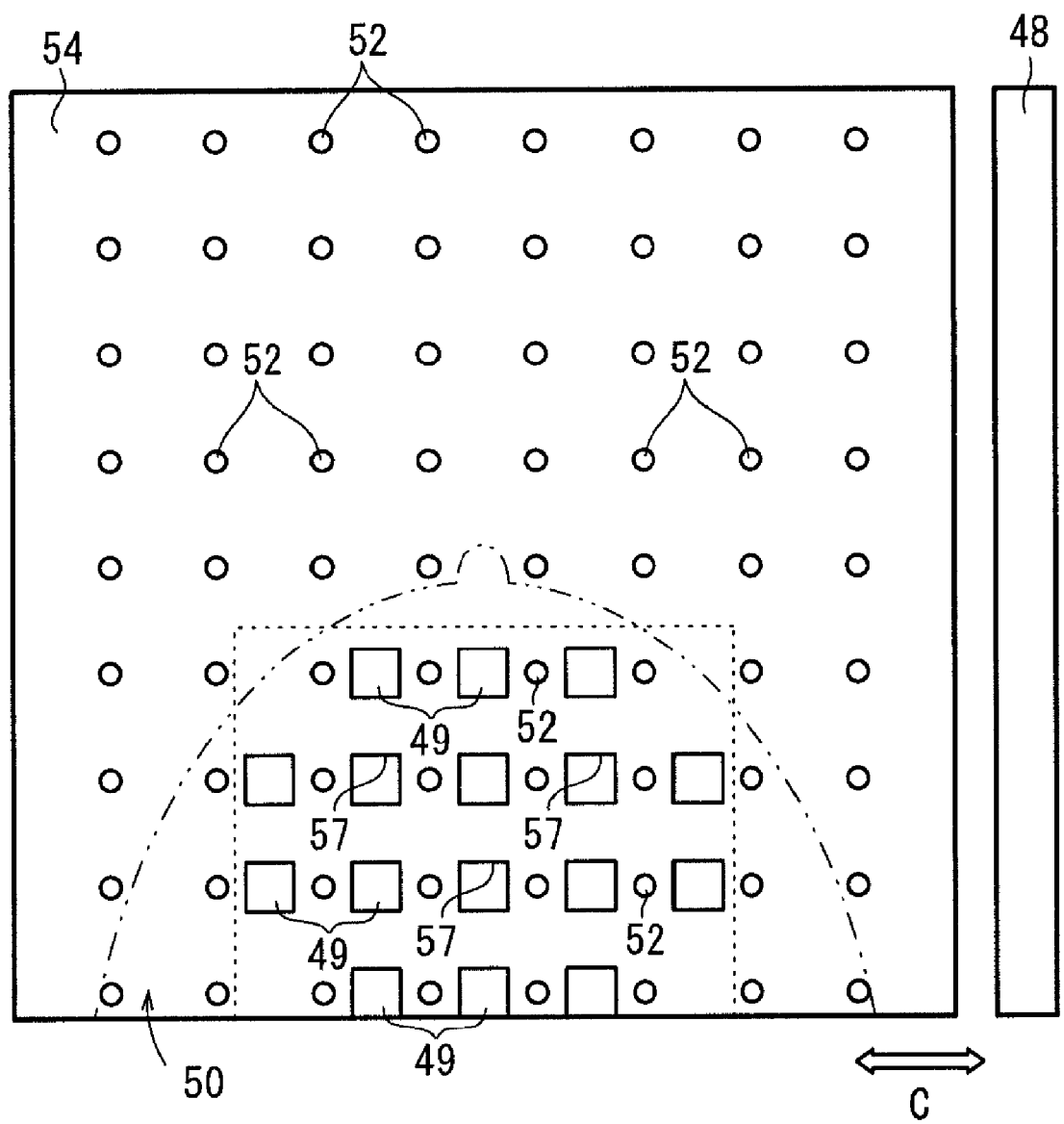
FIG. 4 is a plan view, partially omitted from illustration, of the internal structural details of the image capturing base shown in FIG. 2.

As shown in FIGS. 3 and 4, the erasing light source 50 comprises a plurality of LED chips 52, which can emit and quench light within a short period of time, and which have very short persistence. The LED chips 52 are arrayed in a matrix and mounted on a panel 54. The panel 54 is mounted in the image capturing base 36 parallel to the solid-state detector 46.

As shown in FIGS. 2 through 4, the plurality of AEC sensors 49 (16 in the present embodiment) are mounted on a sensor board 56, and are oriented toward the solid-state detector 46 from respective holes 57 defined in the panel 54. The AEC sensors 49 are surrounded by respective rectangular tubular members (not shown), which extend from the holes 57 toward the AEC sensors 49 along the direction of the radiation X emitted from the radiation source 33.

The AEC sensors 49 are arrayed on the sensor board 56 so as to correspond positionally to the breast 44, which is positioned on the image capturing base 36 (see FIGS. 3 and 4).

Figure 5:
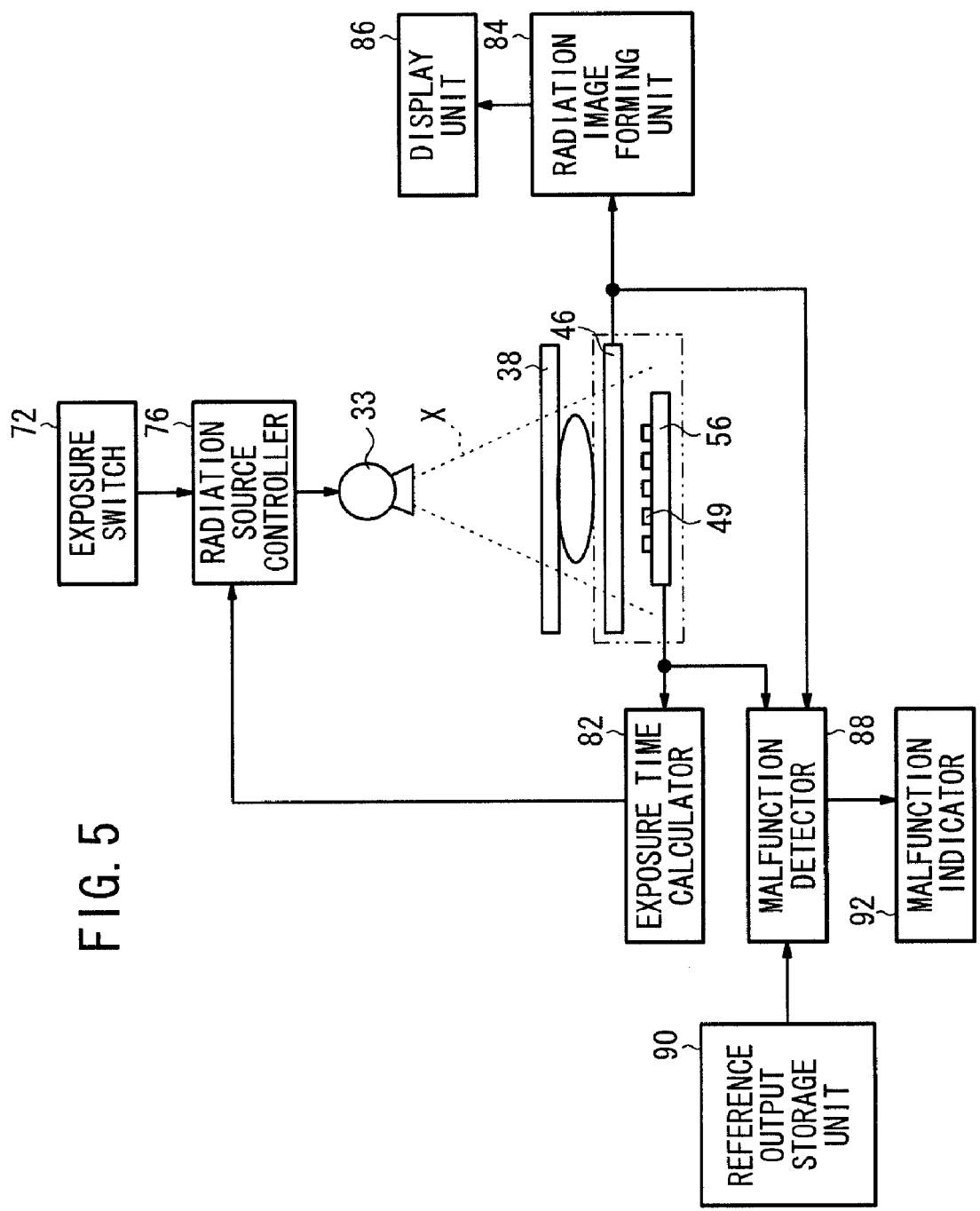
FIG. 5 is a block diagram of a control circuit of the mammographic system shown in FIG. 1.

As shown in FIG. 5, a control circuit of the mammographic system 12 includes a radiation source controller (radiation source control means) 76 housed in the radiation source housing unit 34 for controlling the radiation source 33, so as to emit radiation X when an exposure switch 72 is triggered, and an exposure time calculator 82 for calculating an appropriate exposure time at which the radiation X is emitted from the radiation source 33 based on the radiation dose per unit time of the radiation X detected by the AEC sensors 49, and for supplying the calculated exposure time as an exposure control condition to the radiation source controller 76. The control circuit of the mammographic system 12 also includes a radiation image forming unit 84 for forming a radiation image based on the radiation image information detected by the solid-state detector 46, and a display unit 86 for displaying the generated radiation image. The solid-state detector 46 thus functions as a radiation image generating means both for detecting radiation emitted from the radiation source 33, and for generating a radiation image.

The control circuit of the mammographic system 12 further includes a malfunction detector (malfunction detecting means) 88, which is supplied with output signals from the solid-state detector 46 and the AEC sensors 49 based on the radiation X emitted from the radiation source 33, and which is also supplied with reference output ranges of the solid-state detector 46 and the AEC sensors 49. The reference output ranges are output ranges representing reference ranges at times when the solid-state detector 46 and the AEC sensors 49 are normal. The reference output ranges are stored in a reference output storage unit (reference output storage means) 90.

The malfunction detector 88 compares output signals from the solid-state detector 46 and the AEC sensors 49 with the reference output ranges of the solid-state detector 46 and the AEC sensors 49, which are stored in the reference output storage unit 90. Also, the malfunction detector 88 detects malfunctioning of the solid-state detector 46, the AEC sensors 49, or the radiation source 33 (determines whether there is a malfunction or not), and sends information concerning the detected malfunction to a malfunction indicator (malfunction indicating means) 92.

The mammographic system 12 according to the present embodiment is basically constructed as described above. Next, operations of the mammographic system 12 shall be described below.

Using a console, an ID card, etc., (not shown), an operator, typically a radiological technician, sets ID information, an image capturing process, etc., for the subject 32. The ID information includes information concerning the name, age, sex, etc., of the subject 32. The ID information can be acquired from an ID card possessed by the subject 32. If the mammographic system 12 is connected to a network, the ID information can be acquired from a higher-level apparatus through the network. The image capturing process represents information including a region to be imaged, which is specified by the doctor, an image capturing directive specified by the doctor, etc., which can be acquired from a higher-level apparatus through the network, or entered by an operator through the console. These items of information can be displayed on the display control panel 40 of the mammographic system 12.

Then, the operator places the mammographic system 12 into a certain state according to the specified image capturing process. For example, the breast 44 may be imaged as a cranio-caudal view (CC) taken from above, a medio-lateral view (ML) taken outwardly from the center of the chest, or a medio-lateral oblique view (MLO) taken from an oblique view. Depending on the information of the selected one of these image capturing directions, the operator turns the arm 30 about the swing shaft 28. In FIG. 1, the mammographic apparatus 20 is shown as being set to take a cranio-caudal view (CC) of the breast 44.

Then, the operator positions the breast 44 of the subject 32 with respect to the mammographic system 12. Specifically, the operator places the breast 44 on the image capturing base 36, and thereafter lowers the compression plate 38 toward the image capturing base 36 to hold the breast 44 between the image capturing base 36 and the compression plate 38, as shown in FIG. 2.

After the above preparatory operation has been completed, the operator operates the mammographic system 12 to start to take a radiation image of the breast 44.

First, the mammographic system 12 operates in a mode (hereinafter referred to as a "pre-exposure mode") for determining an exposure control condition for a region of interest (mammary gland region) by setting the radiation dose of the radiation X applied to the breast 44 to a low level. Thereafter, the mammographic system 12 operates in a mode (hereinafter referred to as a "main exposure mode") for applying the radiation X at a radiation dose according to the determined exposure control condition, in order to capture a radiation image of the breast 44.

The radiation source controller 76 controls the tube current supplied to the radiation source 33 so as to set the radiation dose per unit time to a low level. The radiation source 33 applies the radiation X at the low radiation dose to the breast 44.

The AEC sensors 49 detect the radiation dose of the radiation X, which has passed through the compression plate 38, the breast 44, and the solid-state detector 46. The exposure time calculator 82 calculates, as an exposure control condition, an exposure time at which to apply the radiation dose, which is required to obtain appropriate radiation image information of the breast 44, based on the radiation dose per unit time detected by the AEC sensors 49.

Since the radiation X applied to the AEC sensors 49 is partially absorbed by the solid-state detector 46, the radiation dose per unit time detected by the AEC sensors 49 needs to be corrected, so as to represent the radiation dose per unit time that actually reaches the detecting surface of the solid-state detector 46, in view of the attenuation of the radiation X caused by the solid-state detector 46. In the pre-exposure mode, the radiation dose per unit time emitted from the radiation source 33 is set to a low level, as described above. Therefore, the radiation dose per unit time that reaches the detecting surface of the solid-state detector 46 in the pre-exposure mode needs to be corrected, in view of the ratio between the radiation dose per unit time emitted from the radiation source 33 in the pre-exposure mode and the radiation dose per unit time emitted from the radiation source 33 in the main exposure mode.

The exposure time calculator 82 calculates an exposure time for the radiation X, such that an integrated value of the radiation dose per unit time that reaches the detecting surface of the solid-state detector 46, as corrected in view of the above factors, will provide, together with the exposure time, the radiation dose required to obtain appropriate radiation image information. The calculated exposure time is set as an exposure control condition in the radiation source controller 76.

Then, the mammographic system 12 initiates operation in the main exposure mode.

The radiation source controller 76 sets the tube current supplied to the radiation source 33 at a given current, for obtaining a radiation dose per unit time required in the main exposure mode. Then, when the operator operates the exposure switch 72, the radiation source 33, which is controlled by the tube current set by the radiation source controller 76, applies the radiation X to the breast 44. After the exposure time set as an exposure control condition has elapsed, the radiation source 33 stops applying the radiation X to the breast 44.

The radiation dose applied during the main exposure mode may be detected by the AEC sensors 49, and an integrated value thereof may be calculated. If the radiation dose exceeds an allowable level before the set exposure time elapses, then the radiation source controller 76 may control the radiation source 33 to stop applying the radiation X to the breast 44. Therefore, the subject 32 can be prevented in advance from being exposed to an excessive amount of the radiation X, due to a failure in the mammographic system 12.

Radiation X that has passed through the breast 44 held between the compression plate 38 and the image capturing base 36 is applied to the solid-state detector 46 housed in the image capturing base 36. At this time, a radiation image represented by the radiation X that has passed through the breast 44 is recorded in the solid-state detector 46. After the radiation image of the breast 44 has been captured, the reading light source 48 moves in the direction indicated by the arrow C (FIG. 3) along the solid-state detector 46, while applying reading light to the solid-state detector 46. In response to such applied reading light, the radiation image information recorded in the solid-state detector 46 is read into the radiation image forming unit 84, which forms a radiation image based on the radiation image information. The formed radiation image is then displayed on the display unit 86. In order to prepare the solid-state detector 46 to capture a subsequent radiation image, the solid-state detector 46, from which radiation image information has been read, is irradiated with erasing light emitted from the erasing light source 50 in order to remove unwanted electrical charges stored in the solid-state detector 46.

The solid-state detector 46 and the AEC sensors 49 may potentially suffer sensitivity malfunctions, characterized by fluctuations of an output value thereof (an output signal level or an output current value) with respect to an expected value. Such sensitivity malfunctions may cause an output malfunction of the radiation source 33. In the mammographic system 12 according to the present embodiment, the malfunction detector 88 detects malfunctioning of the solid-state detector 46, the AEC sensors 49, or the radiation source 33, whereas the malfunction indicator 92 notifies the operator of the detected malfunction.

A method of detecting a malfunction in a radiation image capturing apparatus according to the present invention shall be described below. Specifically, a method of detecting a malfunction of the mammographic system 12 according to the present embodiment shall be described, as an example of the malfunction detecting method according to the present invention.

The malfunction detecting method may be performed either when the breast 44 is placed on the image capturing base 36 (during the pre-exposure mode or the main exposure mode) or when the breast 44 is not placed on the image capturing base 36. When the breast 44 is not placed on the image capturing base 36, malfunctioning of the solid-state detector 46, the AEC sensors 49, or the radiation source 33, can accurately be detected because the emitted radiation is not absorbed by the breast 44. Conversely, when the breast 44 is placed on the image capturing base 36, it is less time-consuming and troublesome to detect a malfunction of the solid-state detector 46, the AEC sensors 49, or the radiation source 33, because the malfunction can be detected at the same time that a radiation image of the breast 44 is captured. The malfunction detecting method, during a time when the breast 44 is not placed on the image capturing base 36, shall be described below. The malfunction detecting method can similarly be carried out at a time when the breast 44 is placed on the image capturing base 36.

Figure 6:
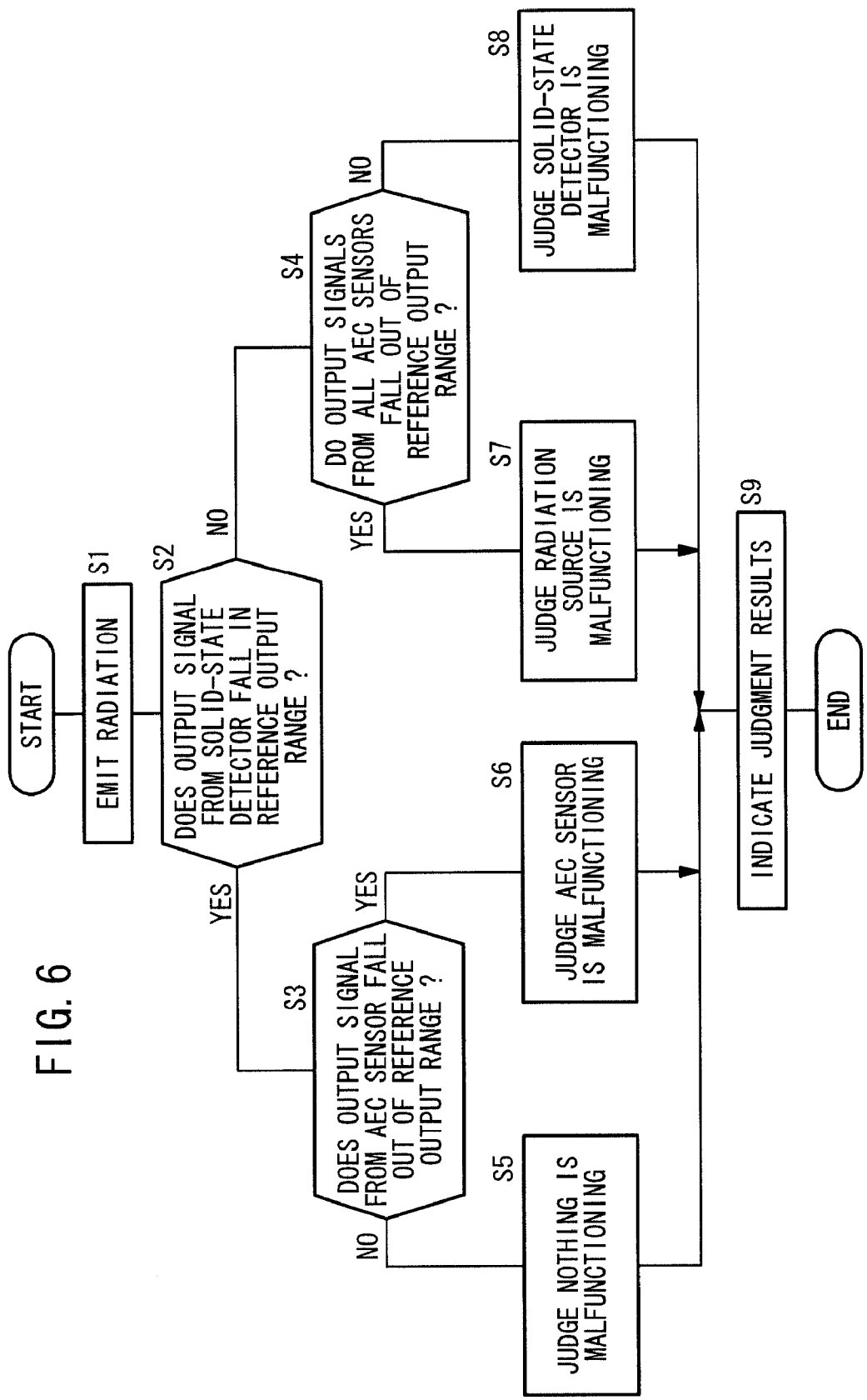
FIG. 6 is a flowchart of a control sequence of a method of detecting a malfunction in the radiation image capturing apparatus according to the embodiment of the present invention, which has a plurality of AEC sensors.

In step S1 shown in FIG. 6, the operator operates a mode selector switch (not shown) on the display control panel 40 in order to change the mammographic system 12 from an image capturing mode to a malfunction detecting mode, and then operates the exposure switch 72. Radiation X emitted from the radiation source 33 is applied to the solid-state detector 46, whereupon radiation image information is recorded in the solid-state detector 46. Also, the radiation dose of the radiation X is detected by each of the AEC sensors 49.

Then, the reading light source 48 moves in the direction indicated by the arrow C (FIG. 4) along the solid-state detector 46, whereby reading light is applied to the solid-state detector 46. In response to the applied reading light, the radiation image information recorded in the solid-state detector 46 is read into the malfunction detector 88. Output signals from the AEC sensors 49 also are applied to the malfunction detector 88.

In step S2, the malfunction detector 88 determines whether or not the output signal from the solid-state detector 46 falls within a reference output range, which is stored in the reference output storage unit 90.

Figure 7:
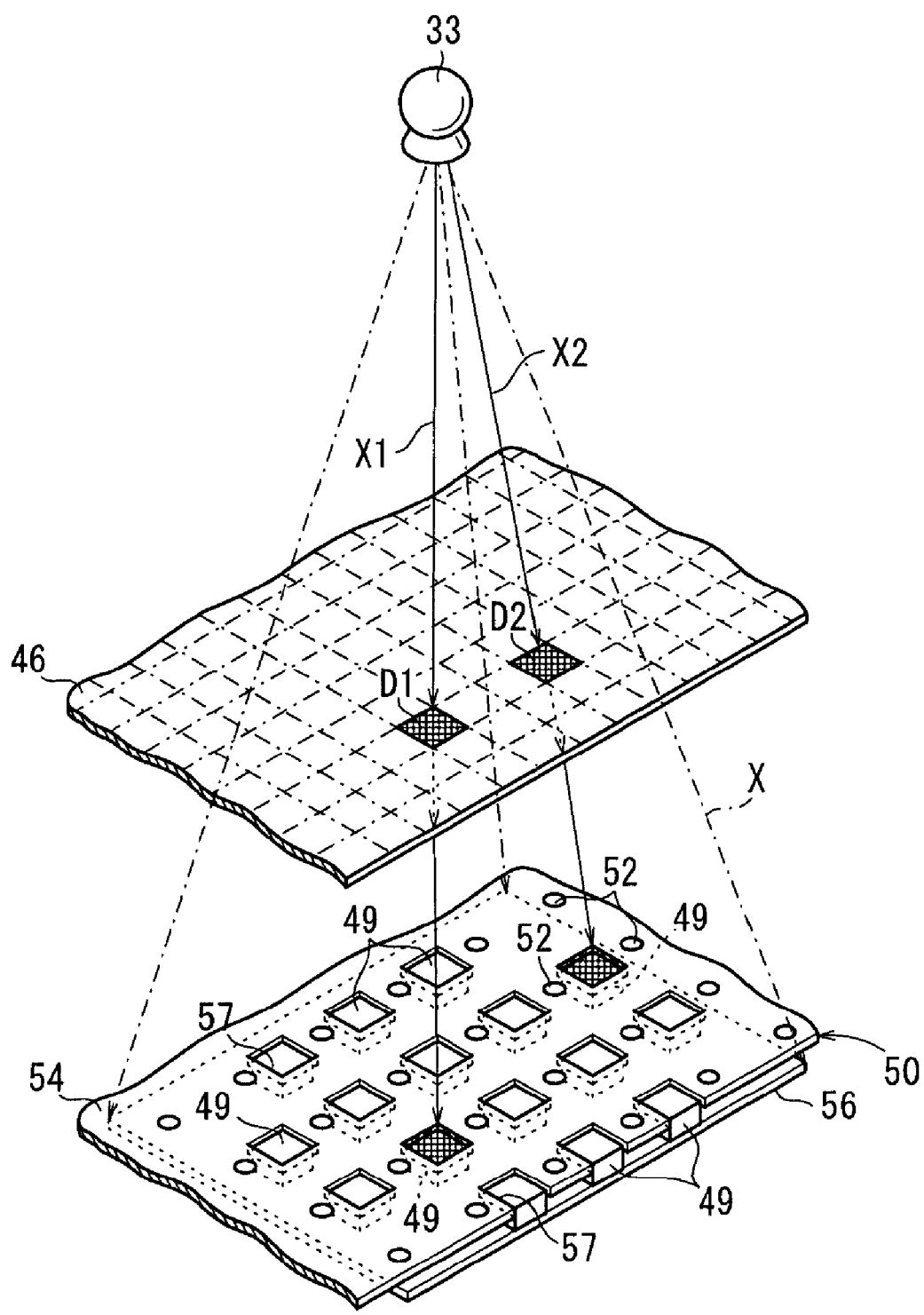
FIG. 7 is a fragmentary perspective view schematically showing a relationship between a radiation source, a solid-state detector, and AEC sensors, in the mammographic system shown in FIG. 1.

The output signal from the solid-state detector 46 represents an output signal (sum value or average value) from the entire surface (all pixels) of the solid-state detector 46, or an output signal (sum value or average value) from a particular region D1 or D2 (see FIG. 7), including a plurality of pixels, of the solid-state detector 46. As shown in FIG. 7, a particular region of the solid-state detector 46 refers to one of a plurality of regions, each including a plurality of pixels therein, into which the entire surface of the solid-state detector 46 is divided.

In step S2, the malfunction detector 88 compares the output signal from the solid-state detector 46, which has detected the radiation X applied to the entire surface thereof, with a stored reference output range corresponding to the entire surface. Alternatively, the malfunction detector 88 compares the output signal from the solid-state detector 46, which has detected radiation X1 and X2 having passed through respective particular regions D1 and D2, with a stored reference output range corresponding to the particular regions D1, D2.

The reference output range is set to a certain allowable range, which is established for a normal output signal in view of fluctuations due to noise or the like, of the output signals from the solid-state detector 46 and the AEC sensors 49. If the output signals from the solid-state detector 46 and the AEC sensors 49 do not suffer from fluctuations, then the reference output range may be set to a single output value.

After step S2, if the output signal from the solid-state detector 46 falls within the reference output range stored in the reference output storage unit 90, then the malfunction detector 88 executes step S3. If the output signal from the solid-state detector 46 falls outside of the reference output range stored in the reference output storage unit 90, then the malfunction detector 88 executes step S4.

In step S3, the malfunction detector 88 determines whether or not the output signals from the AEC sensors 49 fall within a reference output range stored in the reference output storage unit 90. Specifically, the malfunction detector 88 determines whether or not the output signal (sum value or average value) from each of the AEC sensors 49 falls within a reference output range stored in the reference output storage unit 90.

If the sum value or average value of the output signals from the AEC sensors 49 falls within the reference output range stored in the reference output storage unit 90 in step S3, then the malfunction detector 88 judges that neither the solid-state detector 46, the AEC sensors 49, nor the radiation source 33, is malfunctioning in step S5. If the output signal from at least one of the AEC sensors 49 falls outside of the reference output range, then in step S6, the malfunction detector 88 judges that the AEC sensor 49 is malfunctioning, however, that the solid-state detector 46 and the radiation source 33 are not malfunctioning.

In step S4, the malfunction detector 88 determines whether or not the output signals from all of the AEC sensors 49 fall within a reference output range stored in the reference output storage unit 90.

If the output signals from all of the AEC sensors 49 fall outside of the reference output range stored in the reference output storage unit 90 in step S4, then in step S7, the malfunction detector 88 judges that the radiation source 33 is malfunctioning, however, that the solid-state detector 46 and the AEC sensors 49 are not malfunctioning. Normally, it is extremely unlikely for all of the AEC sensors 49 to malfunction at the same time. Therefore, if the output signals from all of the AEC sensors 49 fall outside of the reference output range, then it is more reasonable to judge that the radiation source 33 is malfunctioning, than to judge that the AEC sensors 49 are malfunctioning. If the output signals from all of the AEC sensors 49 fall inside the reference output range stored in the reference output storage unit 90 in step S4, then in step S8, the malfunction detector 88 judges that the solid-state detector 46 is malfunctioning, however, that the AEC sensors 49 and the radiation source 33 are not malfunctioning.

The malfunction detector 88 sends the judgment results in steps S5, S6, S7, S8 to the malfunction indicator 92. The malfunction indicator 92 displays the judgment results on an external display, e.g., a display control panel 40, so as to notify the operator of the detected malfunction. Since the operator can easily identify the part that has been detected as malfunctioning, the operator can quickly replace or repair the malfunctioning part. According to the present embodiment, therefore, malfunctions of the solid-state detector 46, the AEC sensors 49, and/or the radiation source 33, can easily and inexpensively be detected without the need for a separate instrument, such as a radiation dosimeter or the like.

In step S2, and in steps S3 and S4, the malfunction detector 88 preferably should compare the output signals from the solid-state detector 46 and the AEC sensor 49 within the same particular region with the reference output range. Specifically, the malfunction detector 88 compares the output signal from the solid-state detector 46 within the particular range D1, for example, which is irradiated with the radiation X1, as well as the output signal from the AEC sensor 49, which is irradiated with the radiation X1 through the same particular range D1, with the reference output range. Even if the radiation dose from the radiation source 33 varies, the solid-state detector 46 in the particular range D1, and the AEC sensor 49 aligned with the particular range D1, are irradiated with the same radiation X1 through the same particular range D1. Accordingly, when the radiation dose from the radiation source 33 varies, the output signals from the solid-state detector 46 and the AEC sensor 49 vary in synchronism with the radiation dose from the radiation source 33. If the output signals from the solid-state detector 46 and the AEC sensor 49 simultaneously fall outside of the reference output range, then it can be judged that the output signals are varied in synchronism with the radiation dose from the radiation source 33. As a result, it can reliably be judged that the radiation source 33 is malfunctioning.

With a radiation image capturing apparatus such as the mammographic system 12, radiation doses applied respectively to the solid-state detector 46 and the AEC sensors 49 normally become more different from each other, at positions that are progressively spaced from the radiation source 33 as viewed in plan. Furthermore, as described above, the radiation dose applied to the solid-state detector 46 within the particular region D1, as well as the radiation dose applied to the AEC sensor 49 through the particular region D1, are both based on the radiation X1 through the same particular region D1 (see FIG. 7). The reference output storage unit 90 stores reference output ranges for the solid-state detector 46 and the AEC sensors 49, which correspond to respective radiation doses expected within the particular regions D1 as well as other particular regions. Since the output signals from the solid-state detector 46 and the AEC sensors 49, which have detected the radiation passing through the particular regions, can be compared with the corresponding reference output ranges, the actual output signals can be compared with corresponding reference output ranges highly accurately. Accordingly, malfunctions in the solid-state detector 46, the AEC sensors 49, and the radiation source 33, can be detected highly accurately.

The mammographic system 12 according to the above embodiment includes a plurality of AEC sensors 49. However, the malfunction detecting method according to the present invention also is applicable to a radiation image capturing apparatus having only a single AEC sensor 49.

Figure 8:
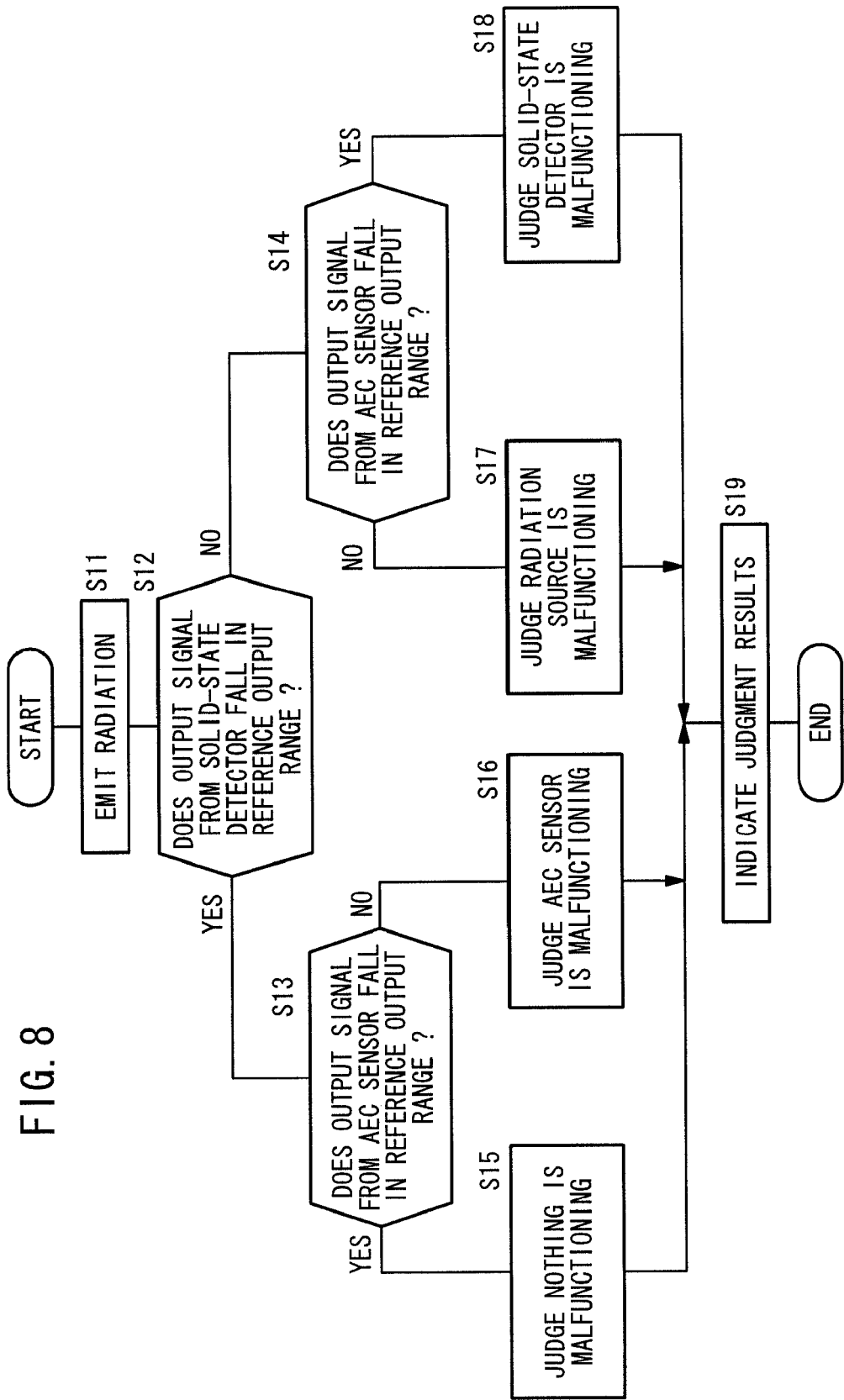
FIG. 8 is a flowchart of a control sequence of a method for detecting a malfunction of the radiation image capturing apparatus, according to the embodiment of the present invention, which has a single AEC sensor.

A malfunction detecting method, applied to a radiation image capturing apparatus having a single AEC sensor 49, shall be described below with reference to FIG. 8.

Steps S11, S12, S19 shown in FIG. 18 are identical to steps S1, S2, S9 shown in FIG. 9 and will not be described in detail below.

If the output signal from the solid-state detector 46 falls within the reference output range stored in the reference output storage unit 90 in step S12, then the malfunction detector 88 executes step S13. If the output signal from the solid-state detector 46 falls outside of the reference output range stored in the reference output storage unit 90, then the malfunction detector 88 executes step S14.

In step S13, the malfunction detector 88 determines whether or not the output signal from the AEC sensor 49 falls within a reference output range, which is stored in the reference output storage unit 90. If the output signal from the AEC sensor 49 falls within the reference output range in step S13, then the malfunction detector 88 judges that the solid-state detector 46, the AEC sensor 49, or the radiation source 33, is not malfunctioning in step S15. If the output signal from the AEC sensor 49 falls outside of the reference output range, then the malfunction detector 88 judges that the AEC sensor 49 is malfunctioning, however, that the solid-state detector 46 and the radiation source 33 are not malfunctioning, in step S16.

If the output signal from the AEC sensor 49 falls outside of the reference output range in step S14, then the malfunction detector 88 judges that the radiation source 33 is malfunctioning, however, that the solid-state detector 46 and the AEC sensor 49 are not malfunctioning, in step S17. If the output signal from the AEC sensor 49 falls within the reference output range in step S14, then the malfunction detector 88 judges that the solid-state detector 46 is malfunctioning, however, that the AEC sensor 49 and the radiation source 33 are not malfunctioning, in step S18.

In the above embodiments, the radiation image capturing apparatus incorporates the solid-state detector 46 therein. However, instead of the solid-state detector 46, the radiation image capturing apparatus may incorporate a stimulable phosphor panel, which is detachably mounted to the image capturing base 36, or a solid-state radiation detector that directly converts an applied radiation into an image, without the need for the reading light source 48.

The radiation image capturing apparatus and the malfunction detecting method according to the present invention are not limited to the mammographic system described in the illustrated embodiment, but also are applicable to a radiation image capturing apparatus for capturing an image of another region, for example the chest, of the subject.

Although certain preferred embodiments of the present invention have been shown and described in detail, it should be understood that various changes and modifications may be made to the embodiments without departing from the scope of the invention as set forth in the appended claims.

What is claimed is:

1. An apparatus for capturing a radiation image, comprising:
    a radiation source for emitting radiation;
    radiation image generating means for detecting radiation emitted from said radiation source, and generating a radiation image based on the radiation;
    a radiation dose information detector for detecting a radiation dose of the radiation emitted from said radiation source;
    radiation source control means for controlling the radiation dose emitted from said radiation source, based on an output signal from said radiation dose information detector;
    reference output storage means for storing reference output ranges defining respective ranges of reference output signals for said radiation image generating means and said radiation dose information detector; and
    malfunction detecting means for comparing output signals generated by said radiation image generating means and said radiation dose information detector based on the radiation emitted from said radiation source, with the respective reference output ranges stored by said reference output storage means, in order to detect a malfunction of any of said radiation image generating means, said radiation dose information detector, or said radiation source; and said malfunction detecting means also judging that neither said radiation image generating means, said radiation dose information detector, nor said radiation source is malfunctioning if the output signal generated by said radiation image generating means falls within the corresponding reference output range, and the output signal generated by said radiation dose information detector falls within the corresponding reference output range; judging that said radiation image generating means is malfunctioning if the output signal generated by said radiation image generating means falls outside of the corresponding reference output range, and the output signal generated by said radiation dose information detector falls within the corresponding reference output range; judging that said radiation dose information detector is malfunctioning if the output signal generated by said radiation image generating means falls within the corresponding reference output range, and the output signal generated by said radiation dose information detector falls outside of the corresponding reference output range; and judging that said radiation source is malfunctioning if the output signal generated by said radiation image generating means falls outside of the corresponding reference output range, and the output signal generated by said radiation dose information detector falls outside of the corresponding reference output range.

2. An apparatus according to claim 1, further comprising: malfunction indicating means for indicating the malfunction detected by said malfunction detecting means.

3. An apparatus according to claim 1, wherein said radiation dose information detector is disposed behind said radiation image generating means along a direction in which the radiation emitted from said radiation source is propagated.

4. An apparatus according to claim 3, wherein said malfunction detecting means compares the output signals generated by said radiation image generating means and said radiation dose information detector based on the radiation dose in the same radiation region, with the respective reference output ranges.

5. An apparatus according to claim 1, wherein said malfunction detecting means compares the output signals generated by said radiation image generating means and said radiation dose information detector based on the radiation dose in the same radiation region, with the respective reference output ranges.

* * * * *